US010182712B2

(12) United States Patent
Matthes

(10) Patent No.: US 10,182,712 B2
(45) Date of Patent: Jan. 22, 2019

(54) CATHETER GUIDED ENDOTRACHEAL INTUBATION

(75) Inventor: Kai Matthes, Berlin, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 1311 days.

(21) Appl. No.: 12/287,894

(22) Filed: Oct. 14, 2008

(65) Prior Publication Data
US 2009/0143645 A1 Jun. 4, 2009

Related U.S. Application Data

(60) Provisional application No. 60/998,729, filed on Oct. 12, 2007.

(51) Int. Cl.
A61B 1/00 (2006.01)
A61B 1/012 (2006.01)
A61B 1/018 (2006.01)
A61B 1/267 (2006.01)
(Continued)

(52) U.S. Cl.
CPC .......... A61B 1/2676 (2013.01); A61B 1/0014 (2013.01); A61B 1/0052 (2013.01); A61B 1/00098 (2013.01); A61B 1/00101 (2013.01); A61B 1/00131 (2013.01); A61B 1/018 (2013.01); A61B 1/0125 (2013.01); A61B 1/267 (2013.01); A61B 1/2673 (2013.01); A61M 16/0486 (2014.02); A61M 16/0488 (2013.01)

(58) Field of Classification Search
CPC ............. A61B 1/0008; A61B 1/00082; A61B 1/00087; A61B 1/00098; A61B 1/00112; A61B 1/00119; A61B 1/00121; A61B 1/00126; A61B 1/00128; A61B 1/00131; A61B 1/00133; A61B 1/00135; A61B 1/0014; A61B 1/00142; A61B 1/00154; A61B 1/005; A61B 1/0051; A61B 1/008; A61B 1/01; A61B 1/012; A61B 1/0125; A61B 1/018; A61B 1/267; A61B 1/2673; A61B 1/2676; A61B 1/233; A61B 1/273; A61B 1/2733; A61B 1/2736; A61M 6/0488; A61M 6/04; A61M 6/0402; A61M 6/0404; A61M 6/0406; A61M 6/0409; A61M 6/0411; A61M 6/0418; A61M 6/0434; A61M 6/0461; A61M 6/0463
USPC ....... 128/200.26, 207.14; 600/104, 106, 107, 600/114–116, 120, 185–199
See application file for complete search history.

(56) References Cited

U.S. PATENT DOCUMENTS 4,573,451 A * 3/1986 Bauman .................. 600/190
4,924,852 A * 5/1990 Suzuki et al. ............ 600/150
5,603,688 A * 2/1997 Upsher .................... 600/190
(Continued)

FOREIGN PATENT DOCUMENTS

DE 10351155 A1 6/2005
GB 2431540 A 4/2007
(Continued)

Primary Examiner — Ryan Henderson
(74) Attorney, Agent, or Firm — McCarter & English, LLP

(57) ABSTRACT

The present invention relates to a guided endotracheal intubation endoscope. A guide catheter is used to position an endoscope and a tube for intubation of a patient. The endoscope can include a steering device for steering the endoscope in at least two directions, as well as suction, irrigation and retraction devices for maintaining a clear field of view.

52 Claims, 11 Drawing Sheets

(51) Int. Cl.
*A61B 1/005* (2006.01)
*A61M 16/04* (2006.01)

(56) References Cited

U.S. PATENT DOCUMENTS

| | | | |
|---|---|---|---|
| 5,665,052 A | 9/1997 | Bullard | |
| 5,842,973 A * | 12/1998 | Bullard | 600/194 |
| 5,846,183 A * | 12/1998 | Chilcoat | 600/136 |
| 5,954,636 A * | 9/1999 | Schwartz et al. | 600/120 |
| 6,221,007 B1 | 4/2001 | Green | |
| 6,679,264 B1 * | 1/2004 | Deem | A61B 17/12022 128/200.24 |
| 6,743,166 B2 | 7/2004 | Berci et al. | |
| 6,761,171 B2 | 7/2004 | Toti et al. | |
| 6,832,986 B2 | 12/2004 | Chhibber et al. | |
| 6,840,903 B2 | 1/2005 | Mazzei et al. | |
| 6,860,264 B2 | 3/2005 | Christopher | |
| 6,887,195 B1 | 5/2005 | Pilvisto | |
| 6,890,298 B2 | 5/2005 | Berci et al. | |
| 6,978,784 B2 | 12/2005 | Pekar | |
| 7,174,889 B2 | 2/2007 | Boedeker et al. | |
| 7,182,728 B2 | 2/2007 | Cubb et al. | |
| RE39,508 E | 3/2007 | Parker | |
| D580,549 S | 11/2008 | Schwartz et al. | |
| 7,458,375 B2 | 12/2008 | Schwartz et al. | |
| 8,079,951 B2 | 12/2011 | Yokota | |
| 2002/0022769 A1 | 2/2002 | Smith et al. | |
| 2003/0168059 A1 * | 9/2003 | Pacey | 128/200.26 |
| 2003/0216616 A1 * | 11/2003 | Krupa | A61B 1/00071 600/140 |
| 2005/0039754 A1 | 2/2005 | Simon | |
| 2005/0085694 A1 * | 4/2005 | Nakao | 600/153 |
| 2005/0268917 A1 | 12/2005 | Boedeker et al. | |
| 2006/0004258 A1 | 1/2006 | Sun et al. | |
| 2006/0095002 A1 * | 5/2006 | Soltesz et al. | 604/39 |
| 2006/0247497 A1 | 11/2006 | Gardner | |
| 2007/0074720 A1 | 4/2007 | Schwartz et al. | |
| 2007/0106121 A1 | 5/2007 | Yokota et al. | |
| 2007/0106122 A1 | 5/2007 | Yokota et al. | |
| 2007/0175482 A1 | 8/2007 | Kimmel et al. | |
| 2007/0185384 A1 * | 8/2007 | Bayer et al. | 600/129 |
| 2007/0287885 A1 * | 12/2007 | Brown | 600/107 |
| 2008/0177146 A1 | 7/2008 | Chen | |
| 2008/0200758 A1 | 8/2008 | Orbay et al. | |
| 2008/0200761 A1 | 8/2008 | Schwartz et al. | |
| 2008/0208000 A1 | 8/2008 | Schwartz et al. | |
| 2008/0287961 A1 * | 11/2008 | Miyamoto et al. | 606/127 |
| 2008/0308098 A1 | 12/2008 | Schwartz et al. | |
| 2009/0090357 A1 | 4/2009 | Schwartz et al. | |
| 2009/0118580 A1 | 5/2009 | Sun et al. | |
| 2010/0095969 A1 | 4/2010 | Schwartz et al. | |
| 2010/0298634 A1 * | 11/2010 | Yanuma | A61B 17/22 600/104 |

FOREIGN PATENT DOCUMENTS

| | | | |
|---|---|---|---|
| JP | 2004154268 A * | 6/2004 | A61B 1/00 |
| WO | WO 99/29228 | 6/1999 | |
| WO | WO 2005/094927 | 10/2005 | |
| WO | WO-2005/094927 A2 | 10/2005 | |

* cited by examiner

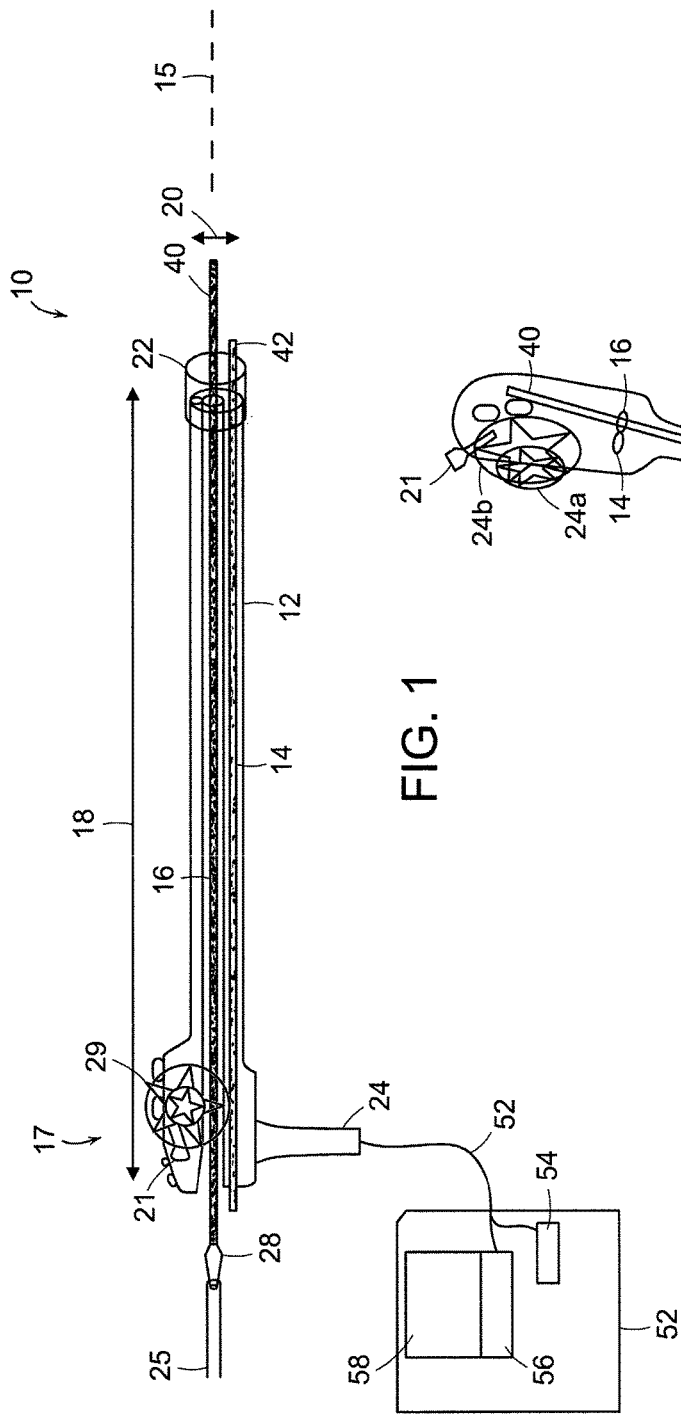
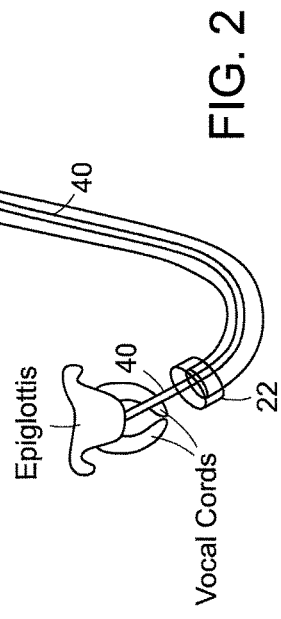
FIG. 1
FIG. 2

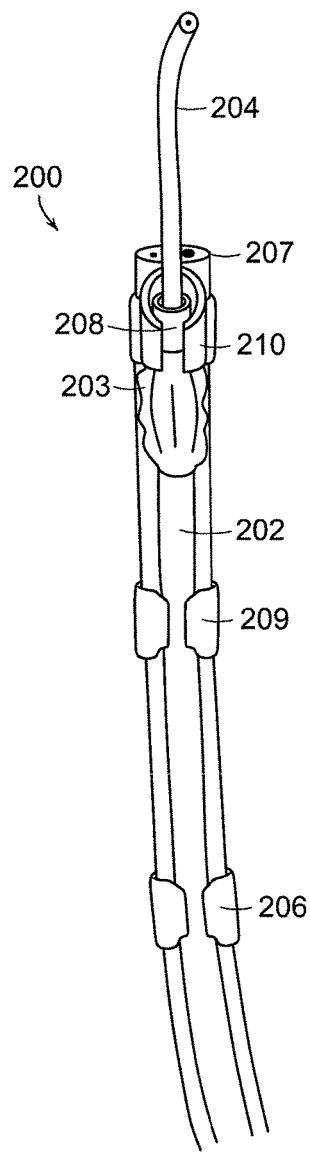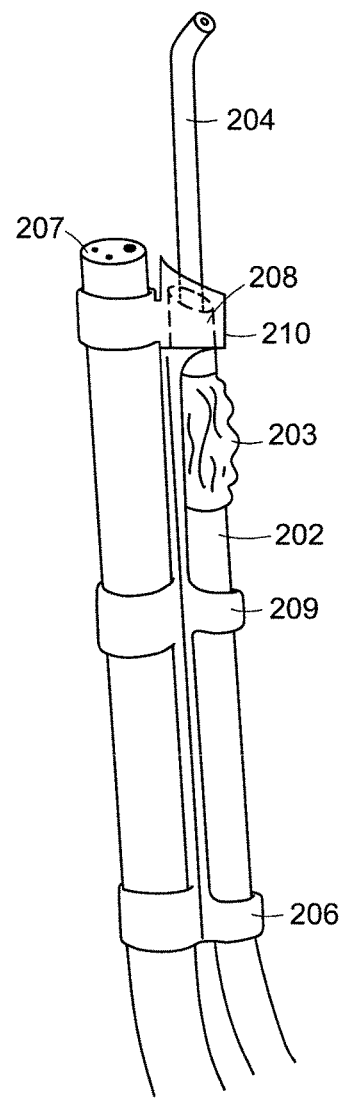
FIG. 11
FIG. 12

CATHETER GUIDED ENDOTRACHEAL INTUBATION

CROSS REFERENCE TO RELATED APPLICATIONS

This application claims priority to U.S. Provisional Application 60/998,729 filed on Oct. 12, 2007, the entire contents of which is incorporated herein by reference.

BACKGROUND OF THE INVENTION

Tracheal intubation is a procedure involving the placement of a tube through the oral cavity, larynx, vocal cords and into the trachea. A laryngoscope is commonly used to view the glottis during placement of the endotracheal tube. The endotracheal tube often has a cuff that is inflated to form a seal with the interior walls of the trachea to prevent aspiration into the lungs.

Endotracheal intubation in patients with a difficult airway is commonly performed using a fiberoptic or video bronchoscope or endoscope. The endoscope is passed through the vocal cords, and once the tracheal rings are identified, endotracheal position of the endoscope is presumed, and the endotracheal tube (ET) is passed blindly through the vocal cords into the trachea until the ET becomes visualized by the lens at the tip of the endoscope. The blind delivery of the tube into the trachea cn result in injury to the vocal cords, particularly in the case of a partially obstructed airway.

Current endoscopes used for endotracheal intubation have a small diameter of 4-5 mm so that an ET tube can be fed onto the endoscope, and then guided by the endoscope into the trachea. These fiberoptic scopes have only one (vertical) angulation direction. To change the direction of the endoscope in the horizontal direction, body movement is used. This limited steerability and the small diameter makes the handling of the endoscope in patients with a difficult airway frequently difficult as the maneuverability of the tip is limited and the tip of the scope is frequently deflected by the tissue.

Thus, there is a continuing need for improvement in devices for endotracheal intubation, particularly for difficult airway intubation.

SUMMARY OF THE INVENTION

The present invention relates to systems and methods for endoscopic visualization of intubation using a guide device such as a catheter or endoscope for a procedure referred to herein as guided endotracheal intubation. A preferred embodiment of the invention includes the introduction of an imaging endoscope into the oropharynx of a patient's airway to provide direct visualization of the tracheal entry region. A guide device can be used to deliver an endotracheal tube that is placed into the trachea under direct visualization with the imaging endoscope. The guide device and/or the intubation tube can also be guided into position using the imaging endoscope at which point the guide device or endotracheal tube can be separated from the imaging endoscope for delivery of the endotracheal tube into the trachea.

An intubation endoscope in accordance with a preferred embodiment of the invention can include an imaging endoscope and a guide catheter or guide endoscope within a working or guide channel which can separate from the external wall of the endoscope. In another embodiment, the guide catheter or guide endoscope can be coupled to an external wall of the imaging endoscope with a coupling device, such as a track or holder.

This method of endotracheal intubation has the advantage that the airway is continuously visualized during the intubation procedure. A working channel of the endoscope (preferably greater then 3 mm) provides for suctioning of fluid (blood, aspirate etc.) from the oropharynx. Most importantly, the tip of the endoscope is stiffer and easier to control than the tip of existing bronchoscopes. This helps to overcome anatomical abnormalities in patients with a difficult airway. To retrieve fluids from the pharynx, the guide device can be connected to a suction device. The lumen of the guide device may also be used to irrigate by connecting a flush syringe to the catheter, or to insufflate oxygen by connecting the catheter or endoscope to an oxygen delivery source. Alternatively, the guide device can have a first lumen to flush or insufflate and a second lumen for suction.

Gastrointestinal endoscopes have a larger diameter of 8-12 mm, two angulation degrees (horizontal and vertical) and one to two large 2.0-3.6 mm working channels. The two angulation directions and the larger diameter facilitate the maneuverability of the endoscope. Most importantly, the larger working channels improve the ability to retrieve fluids from the oropharynx significantly. Gastroscopes provide the possibility to irrigate the lens continuously by using the flush button of the endoscope. To flush away objects more effectively, a fluid containing syringe can be connected to the working channel of the endoscope.

However, endoscopes with large diameter working channels, as used for gastrointestinal endoscopy, make it impossible to feed an endotracheal tube on the endoscope as is done with existing endotracheal endoscopes. Existing endotracheal endoscopes are often not sufficiently stiff in situations involving an obstructed airway, are not sufficiently steerable and often have lower resolution and a reduced field of view.

In another preferred embodiment of the invention, a smaller imaging endoscope and a small diameter guide device and endotracheal tube can be used for pediatric applications in which the critical anatomical features have smaller dimensions.

For the purpose of catheter guided intubation, instead of fitting the endotracheal tube over the endoscope, a 14 French guide catheter is introduced into the working channel of the endoscope. The guide catheter or endoscope can include stiffening elements or filaments or a braided tubular body to provide a desired level of stiffness and can also be steerable with a bendable distal portion. It is preferred that the guide catheter or second (guide) endoscope have a distal bending region that readily bends to conform to the distal bend of the imaging endoscope during steering. The endotracheal tube can also have a bendable section, particularly for embodiments in which the tube is attached to the distal end of the imaging endoscope.

The endotracheal (ET) tube is then advanced into the trachea by the guidance of the catheter. During this maneuver, the intubation of the vocal cord can be directly visualized by the endoscope, which is positioned in the oropharynx keeping the vocal cords in view of the optical lens at the distal end of the endoscope.

The use of a clear distal cap on the tip of the endoscope, facilitates the visibility as it helps to keep tissue at a fixed distance from the lens instead of obstructing the view.

The guide catheter or guide endoscope can include fiber optic cables that deliver illuminating light and collect images to provide for visualization within the trachea during insertion of the endotracheal tube. The optical fibers associated with light delivery and collection are optically coupled to a light source and a two dimensional imaging detector. The detector can be positioned in the handle of one or both endoscopes, at the distal end of one or both endoscopes, or alternatively, in the processor housing. In the case of a fiber optic catheter, the fiber optics can be coupled to a detector in a second processor housing.

In a preferred embodiment, images from both the imaging endoscope and the guide endoscope or catheter can be displayed simultaneously on the same display, either side by side or with a screen with a screen. The use of two images of different regions within the airway can facilitate safe delivery even where obstruction would usually be a substantial impediment.

BRIEF DESCRIPTION OF THE DRAWINGS

FIG. 1 is a schematic view of an endotracheal intubation endoscope in accordance with the invention.

FIG. 2 is a schematic perspective view of a airway management endoscope positioned relative to the vocal cords.

FIGS. 11-14 illustrates a coupling device to couple an endotracheal tube delivery device to an endoscope and release thereof in accordance with preferred embodiments of the invention.

DETAILED DESCRIPTION OF THE INVENTION

Figure 3A:
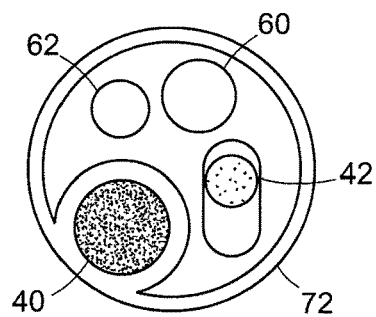
FIG. 3A-3C illustrate cross sectional views of a guided endotracheal intubation endoscope in accordance with preferred embodiments of the invention.

The present invention comprises an endotracheal endoscope 10 as illustrated in the schematic view of FIG. 1. The endoscope 10 has a flexible tubular body 12 extending along a central axis 15 with a first channel 16 in which a guide catheter 40 can be inserted. The endoscope 10 can have a width 20 in a range of 8-14 mm, preferably about 12 mm, and a length 18 in a range of 200-600 mm, preferably about 300-400 mm. The distal end of the endoscope can have a transparent distal window or clear cap 22 which can be retracted using a button at the proximal end control device 17. The control device can include a steering device or wheel 29, or two separate wheels, to control the direction of the distal end in two orthogonal directions. A second channel 14 can be used with a retraction catheter 42. The endoscope can be connected to a light source via a fiber optic cable 52 that extends from a light source 54 to the distal end of the endoscope where it is used to illuminate the field of view.

The processor cable 24 can also include a connecting cable extending from a distally mounted imaging detector on the endoscope to a processor 56 contained in housing 52. A display 58 is used to display images or video from the region being viewed.

The guide catheter 40 can include a hollow lumen that can be connected to a suction tube 25 with an adapter 28 or to an oxygen delivery source. The channel 14 allows the insertion of a retraction catheter 42 that is used to move or lift the epiglottis, shown in FIG. 2.

Figure 3B:
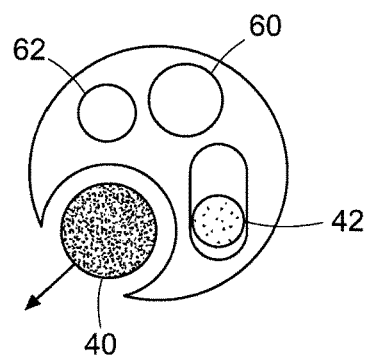
Figure 3C:
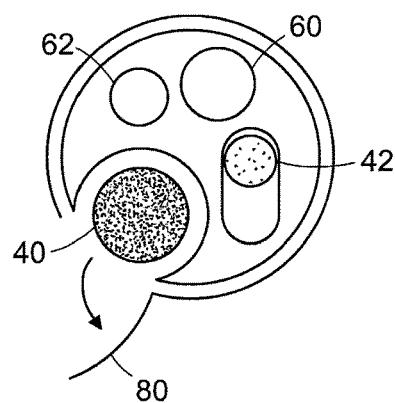

A preferred embodiment of the invention includes an endoscope with a release mechanism that releases the guide catheter from the endoscope without the need for withdrawing the endoscope as shown in FIGS. 3A-3C. The release of the guide catheter is facilitated by a working channel that opens to the side, the opening extending along the length of the endoscope from the insertion port of the working channel to the distal section of the endoscope. After the guide catheter is advanced through the vocal cords, it can be taken out of the working channel to the side, and the ET can be guided into the airway while the endoscope is maintained in the oropharynx facing the vocal cords. Before the release, the guide catheter can be kept inside of the working channel by an overtube 72 as shown in FIG. 3A, which is removed, as shown in FIG. 3B, to set the catheter free. Alternatively a locking mechanism can be used with a panel 80 to open the working channel to the side electrically or mechanically by operating a switch, button or lever as seen in FIG. 3C. Alternatively, the endotracheal tube can be fixed by a rubber lip or snaps holding the tube in place inside the working channel with a lateral opening. The user can move the tube laterally for release. The light from the light source is emitted through aperture 62 and a lens 60 at the distal end collects light to provide the desired image of the region.

Currently available gastroscopes can be used to perform an endotracheal intubation. Due to their increased length of approximately 100 cm in comparison to bronchoscopes with a length of approximately 60 cm, a guide catheter can be used having a length of approximately at least 140 cm and preferably about 160 cm. The characteristics of the guide catheter are those of endotracheal tube exchange catheters, but with an increased length. In one embodiment, two Airway Exchange Catheters (AEC, Cook Inc., Bloomington, Ind.), each 80 cm long, can be connected end-to-end with tape or other connecting material or devices to achieve a combined length of 160 cm in order to overcome the increased length of the gastroscope (100 cm). The proximal Rapi-Fit adapter of the airway exchange catheter can be connected to a three-way stopcock, which is connected by a 14 FR suction catheter T-piece to wall suction. A 20 ml syringe, connected to the stopcock, can be used to irrigate the oropharynx. The gastroscope was advanced into the oropharynx with the AEC introduced into the working channel of the endoscope. Once the airway was identified, the AEC was advanced through the vocal cords into the trachea under endoscopic view. Keeping the AEC in the trachea, the endoscope was withdrawn and reinserted alongside the AEC. A 7.0 mm ET tube was advanced over the AEC into the trachea under direct visualization.

One disadvantage of this method, as described above, the endoscope needs to be withdrawn to separate the guide catheter from the endoscope before the catheter can be used to guide the endotracheal tube through the vocal cords into the airway. The endoscope needs to be reinserted alongside the guide catheter to observe the endotracheal intubation. In some patients this step may be omitted as the guide catheter can be used clinically to intubate the trachea blindly without endoscopic visualization. However, the observation of the intubation step provides an enhanced safety feature particularly for patients presenting more difficult issues for intubation.

In a preferred embodiment of the invention, instead of using a guide catheter, a small diameter endoscope such as a bronchoscope or fiber optic catheter can be used to direct the ET into the airway. Thus catheter 40 can also be a smaller endoscope that is inserted side by side with endoscope 10. The image of the second smaller endoscope can be displayed on the same monitor or display screen next to the image of the first larger endoscope such as a screen-in-screen technique. This provides for visualization of the vocal cords and the inside of the trachea at the same time. The length of the smaller endoscope can be about 200-400 mm longer than the large endoscope that can have a length 200-600 mm, for example, thus providing a smaller diameter endoscope that is longer than 500 mm, preferably about 700-800 mm. The diameter of the second smaller endoscope is preferably at least 1 mm smaller than the working channel 16, preferably about 2-3 mm in diameter. Existing pediatric bronchoscopes, for example, have dimensions suitable for use. Once the smaller endoscope is positioned correctly adjacent the first endoscope the ET tube can be inserted along the second endoscope.

This method for intubation is applicable in patients with a history of a difficult intubation or an airway assessment that is associated with a difficult intubation (Mallampati class IV airway, limited range of motion of the neck, prominent upper teeth, limited mouth opening etc.). It is particularly helpful in trauma patients who require intubation while the neck is immobilized (inline neck stabilization). In these patients, the limited possibility to extend the neck makes the intubation with a regular laryngoscope difficult and sometimes impossible, especially if other anatomical airway abnormalities are present (short neck, prominent upper incisors, obesity, soft tissue swelling). For these reasons, a fiberoptic intubation of the trachea is frequently chosen. However, in the case of orofacial trauma, repeated intubation attempts with a regular laryngoscope, significant bleeding in the oropharynx may occur, which can make the standard fiberoptic technique impossible.

The suction of the regular bronchscope is frequently insufficient to retrieve blood effectively. With the present method, any liquids in the oropharynx can be suctioned sufficiently by connecting the endoscope or guide catheter for suctioning such as wall suction.

Figure 4:
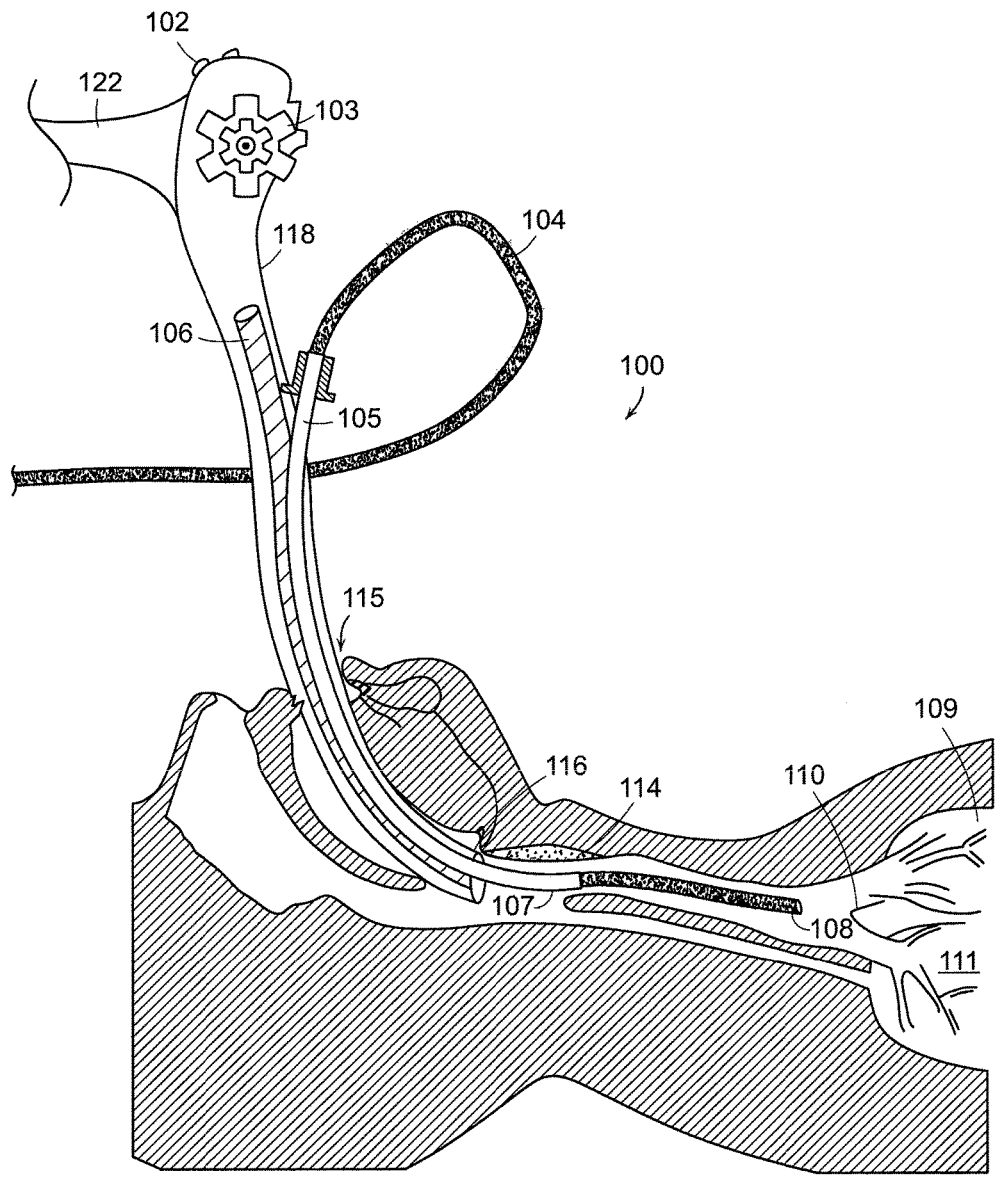
FIG. 4 illustrates use of an endotracheal intubation endoscope system in accordance with a preferred embodiment of the invention.

Illustrated in FIG. 4 is an endotracheal intubation system 100 in accordance with another preferred embodiment of the invention. The system 100 includes a tubular endoscope body 118 with a handle portion having vertical and horizontal steering controls 103, a control panel 102 having control switches, such as a freeze image switch to prompt the display between static and video imaging, and a suction insufflations button. A cable 112 can connect the handle portion to image data storage, processor and an electronic display. The distal end 116 of the endoscope body can have a distal optical system for imaging of the region, such as the vocal cords and the entry into the trachea 114. The endoscope body 118 has a working channel in which a portion of a guide catheter or guide endoscope 104 can be inserted. In this embodiment, the working channel can be opened to release the portion of the guide device 104, the distal end 108 of which has already been inserted through the tracheal entry 114 and positioned adjacent to the carina.

In the embodiment in which catheter 104 comprises a fiber optic viewing device, this provides for viewing of the bifurcation of the trachea into the left and right mainstem bronchus. Correct placement of the endotracheal tube 105, which is inserted into the oral cavity 115, guided by the guide device 104, into the trachea can be confirmed with the image collected at 108 displaying the bifurcation of the left and right bronchus. The use of the imaging endoscope 118 along with imaging provided by the guide device 104 provides for simultaneous viewing of both the entry into the trachea to view placement and inflation of the intubation tube cuff 107 and the bifurcation of the trachea into the left lung 109 and right lung 111.

Figure 5:
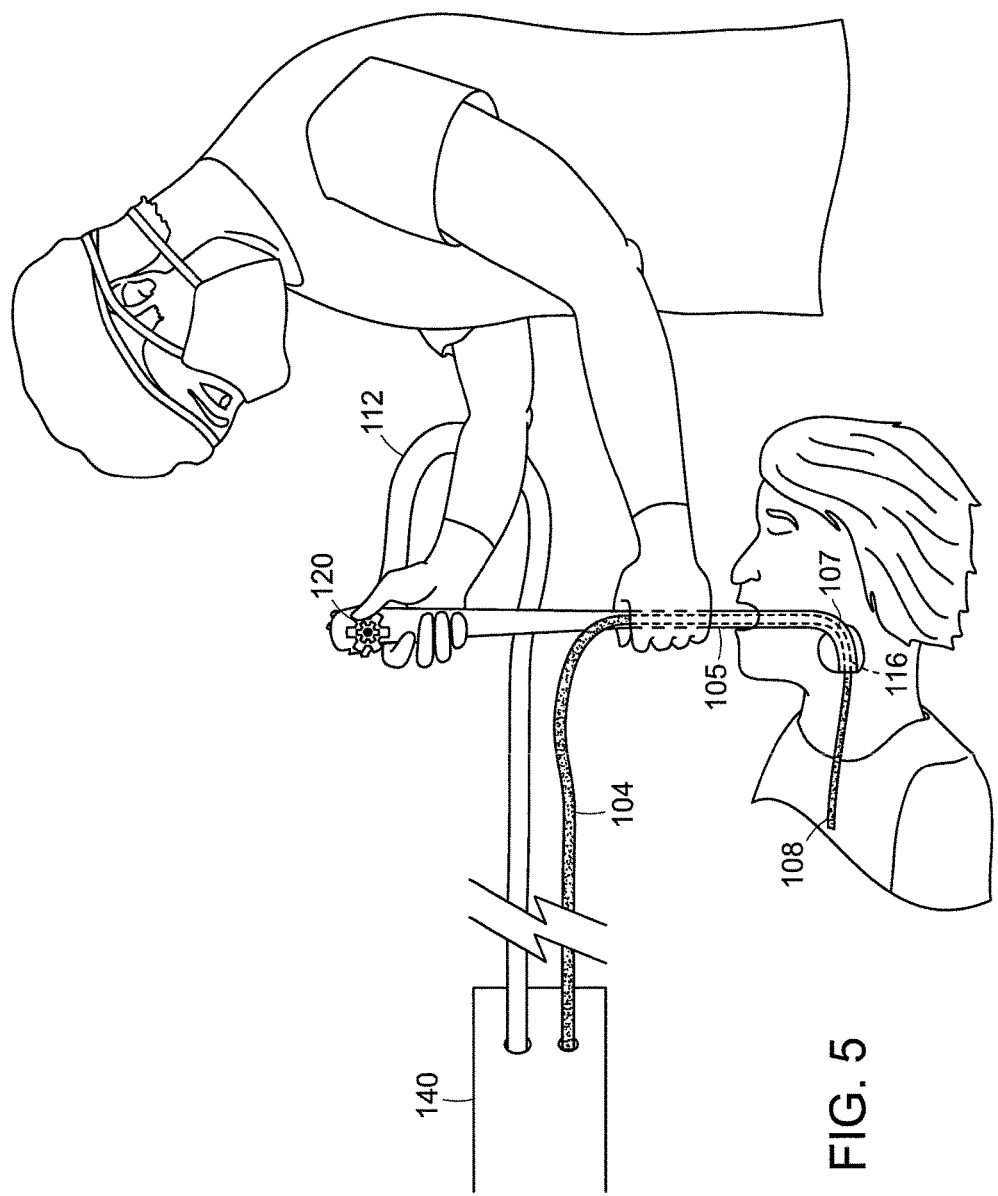
FIG. 5 illustrates an endotracheal intubation endoscope system in accordance with preferred embodiments of the invention.

Illustrated in FIG. 5 is the use by the physician or other user in which one hand grasps the handle 120 of the endoscope and the remaining hand grasps the tube 105 and/or catheter 108. In this embodiment, both the fiber optic catheter or endoscope 104 and the endoscope cable 112 can be connected to the processor housing 140. The processor housing 140 can include a first and second electronic imaging device, such as CCD or CMOS imaging devices. The first imaging device detects light collected by the fiber optic imaging cable of the imaging endoscope and the second imaging device detects light collected by the imaging fiber optic cable 104. Alternatively, the first imaging device can be positioned within the handle 120. In this embodiment, a wireless connection can be used between the handle 120 and a receiver in the processor housing 140.

Figure 6:
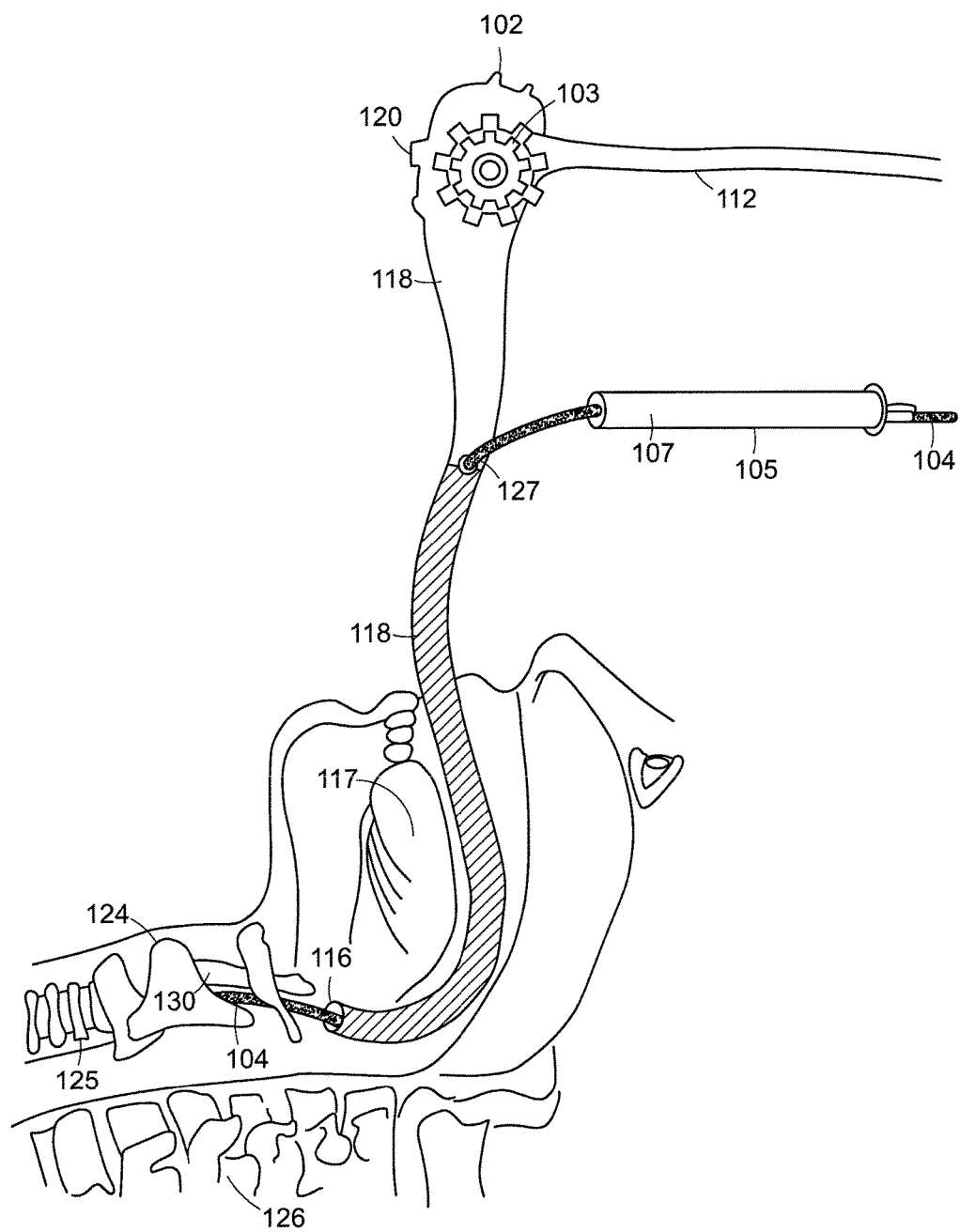
FIG. 6 illustrates the anatomical features impacting intubation of a patient.

Illustrated in FIG. 6 is the insertion of catheter 104 through the proximal entry port 127 into the enclosed working channel 106. The endoscope is inserted over the tongue 117 to view the epiglottis 130, and the trachea 125. The epiglottis 130 can be lifted up with the guide device to display the vocal cords and the entry into the trachea.

In patients with airway obstruction from tumors or swelling from inflammation or trauma (e.g. to the thyroid cartilage 124 or vertebrae 126) correct display of the vocal cords can be challenging. The guide device can be used to bypass strictures or move objects or structures out of the way to display the vocal cords and intubate the trachea.

Figure 7:
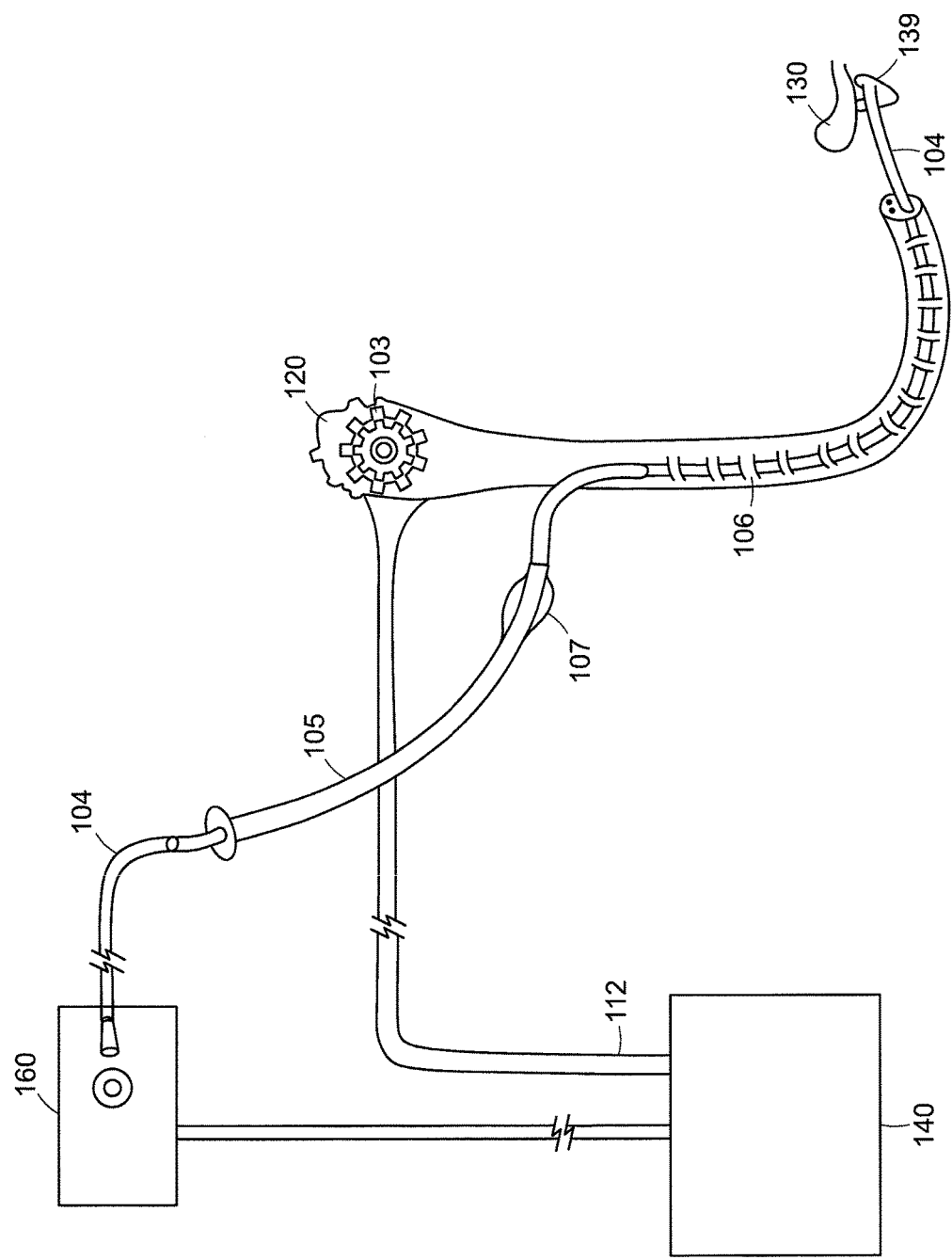
FIG. 7 illustrates a preferred embodiment of the invention utilizing a guide catheter in an endoscope working channel.
Figure 8:
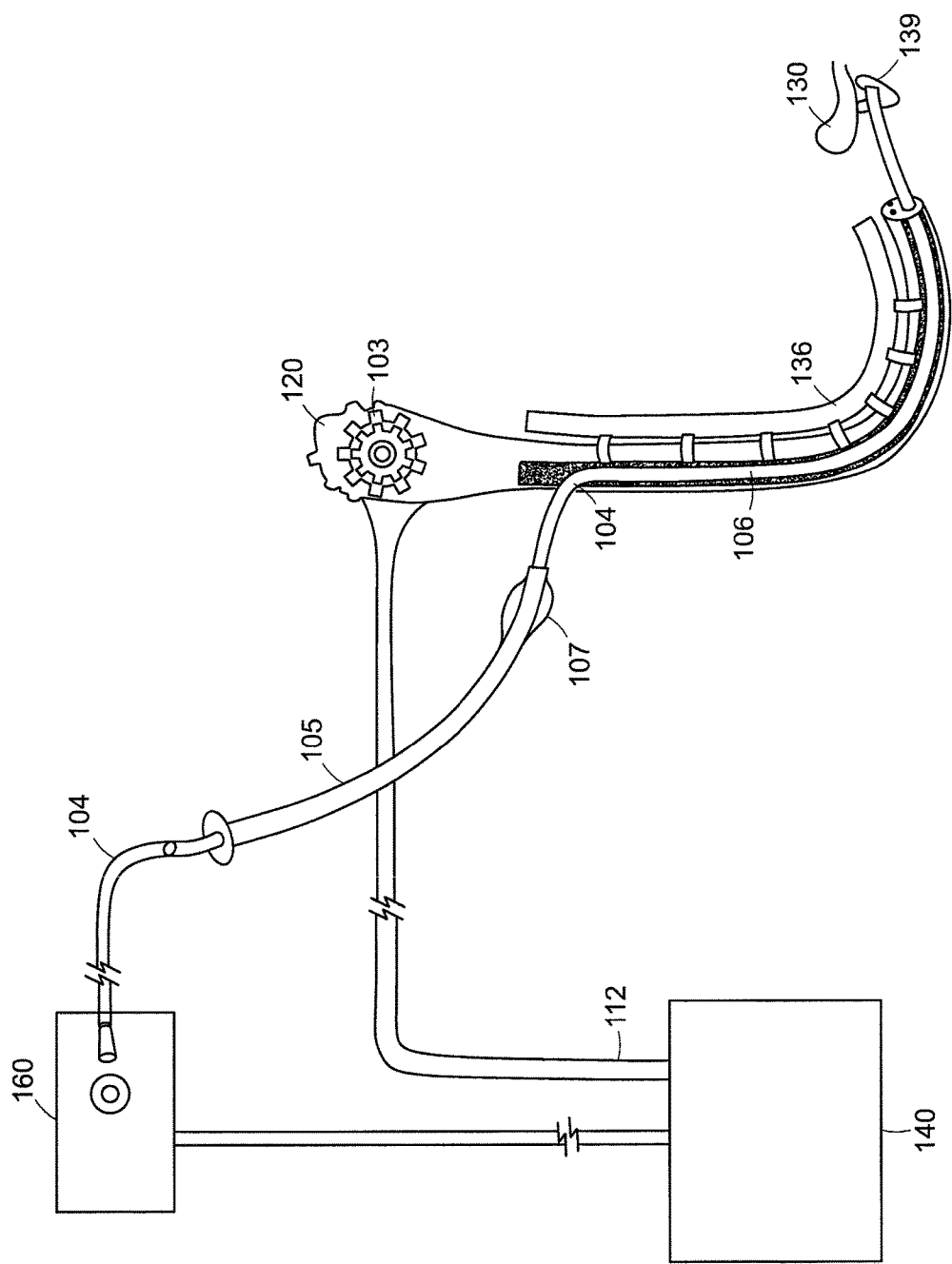
FIG. 8 illustrates opening of the working channel to separate a guide catheter or guide endoscope from the imaging endoscope.
Figure 9:
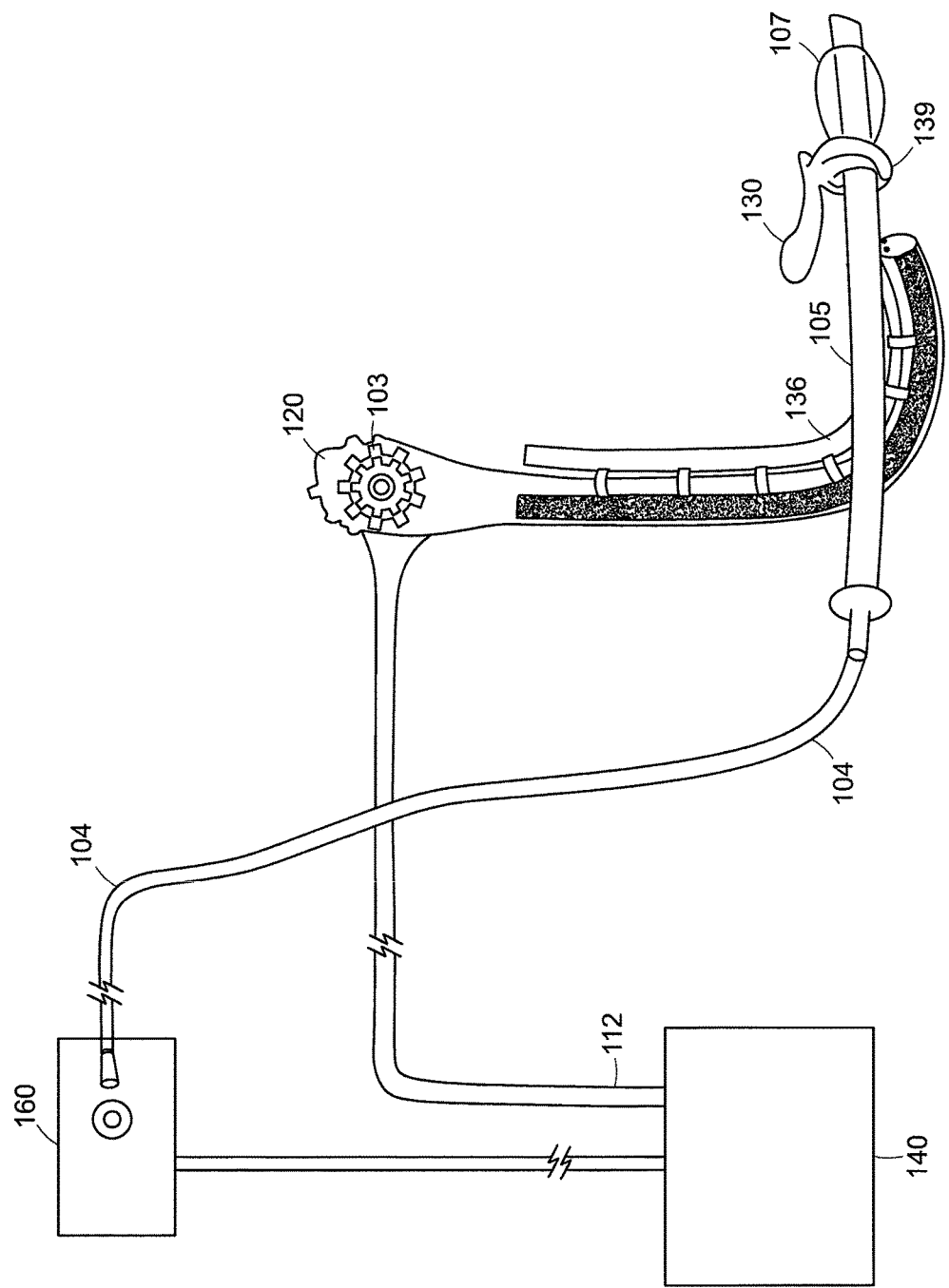
FIG. 9 illustrates delivery of the endotracheal tube using the separated guide device.

Shown in FIG. 7 is an embodiment in which the smaller guide device 104, extending past vocal cords 139, comprises a small diameter endoscope having a separate processor housing 160 that can be connected to the proximal end. The smaller endoscope has a separate light source and imaging detector in housing 160 and can have a second control panel with separate switches to control imaging, suction and insufflation functions of endoscope 104. In FIG. 8, the working channel 106 has a panel 136 that moves to open the working channel so that the catheter or endoscope 104 can be removed and allow the tube 105 to be inserted into position alongside endoscope 118 as shown in FIG. 9.

Figure 10B:
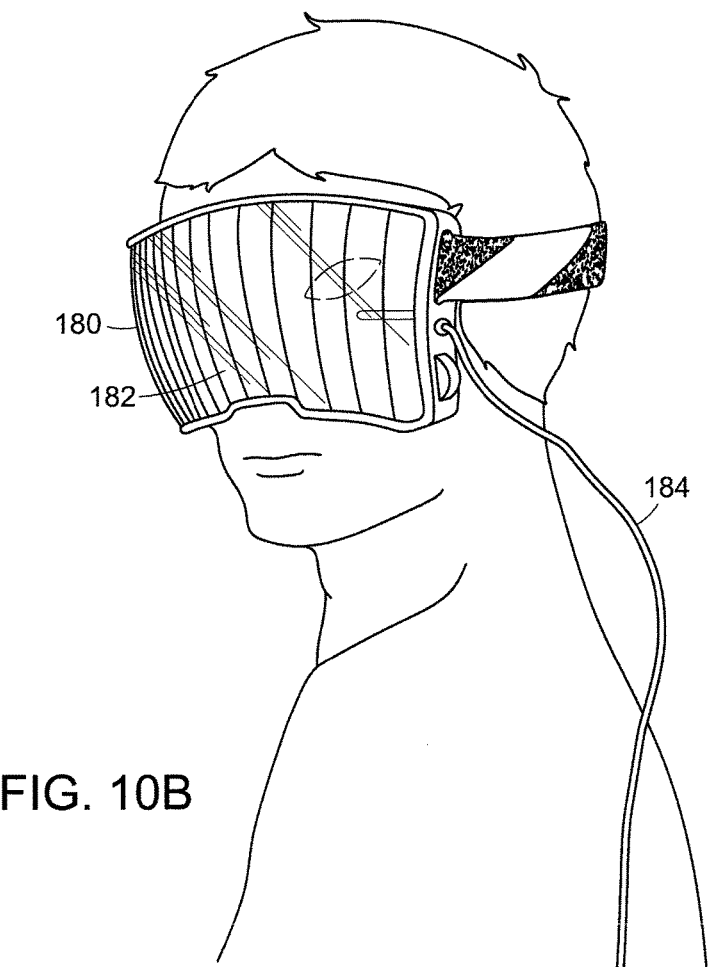
FIGS. 10A and 10B illustrate display systems used in accordance with the invention.
Figure 10A:
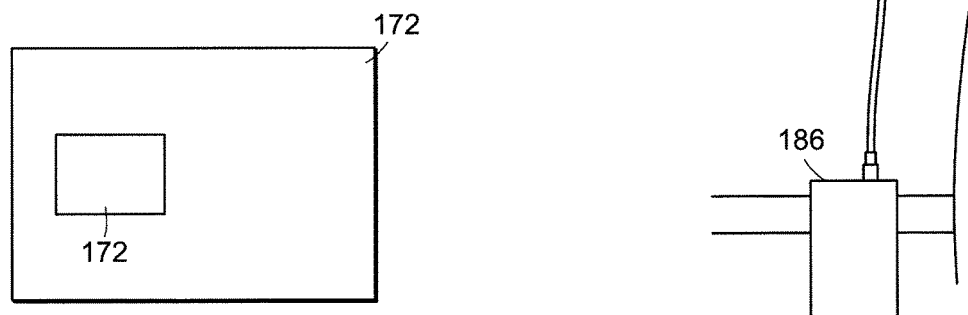

Shown in FIG. 10A is a display for a preferred embodiment of the invention in which the image detected by the first imaging device is shown in first display region 172 and the image detected by the second imaging device can be shown simultaneously in second display region 172. A head mounted display device 180 as shown in FIG. 10B can have a display device 182 connected by cable 184 to wireless or wired connection port 186 worn by the user. The display device 182 can incorporate the screen in screen technology illustrated in FIG. 10A. A retraction catheter can also be inserted to move tissue within the field of view and thereby accommodate safe delivery of the tube into the trachea.

In another preferred embodiment, the guide catheter is attached to the side of the imaging endoscope with a coupling device, such as a track or holder during insertion and positioning of the endoscope to view the vocal cords. The guide catheter is then detached and the endotracheal tube is then inserted along the guide catheter into position. Shown in FIGS. 11-14 is a preferred embodiment of the system 200 in which the endotracheal tube 202 is attached to the imaging endoscope 207 using a coupling device, such as a track or a plurality of holder elements. In this embodiment, snap-on elements 206, 209, 210 are used to hold the endotracheal tube 202 at the distal of the endoscope 207. The optional cuff 203 can be situated between elements 209 and 210, for example, which can connect the endoscope to the endotracheal tube, i.e. the holders attach on first and second portions of the tube on different sides of the cuff. The holder elements are positioned along the steerable portion of the endoscope such that when the distal end of the endoscope is bent, the tube 202 has a bending region also bends to conform to the curved shape of the endoscope. A guide catheter 204 can also be used with the older elements 206, 209, 210 or a track facilitate positioning of tube 202.

Figure 13:
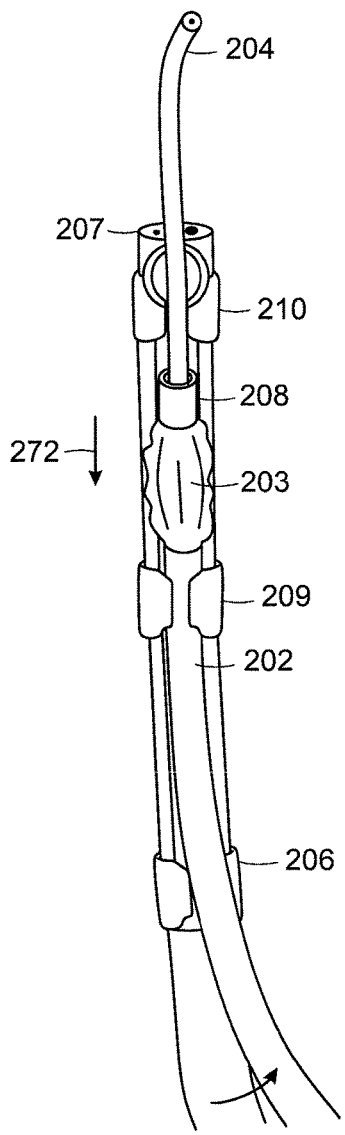
Figure 14:
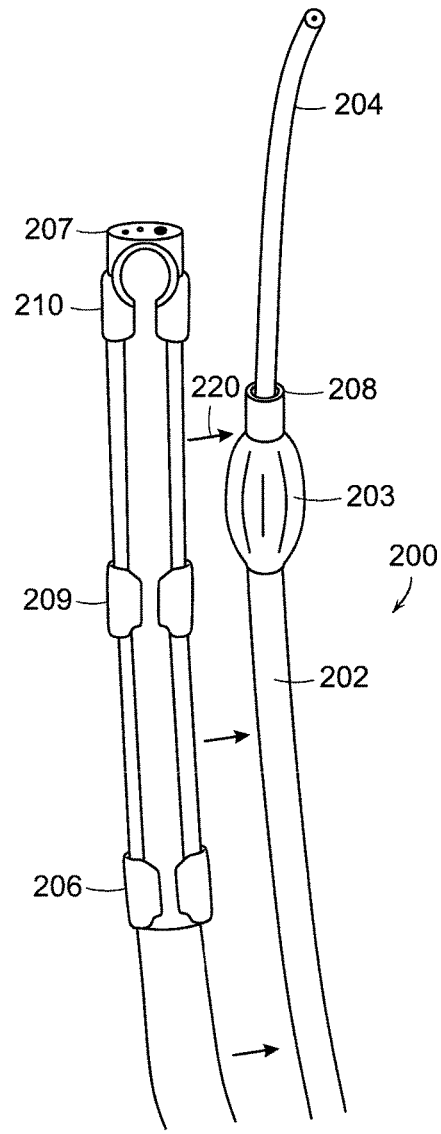

FIGS. 11 and 12 show front and side views of the system 200 with the tube 202 attached to the endoscope 207. In FIG. 13, the tube 202 can be moved in a proximal direction 212 relative to the endoscope to enable release 220 of the tube 202 from the holder as shown in FIG. 14. an actuator mechanism can be operated by the user, such as a pull wire, to release the tube.

In a preferred embodiment of the invention, the endotracheal intubation system comprises a pediatric intubation system in which the dimensions and physical strength of the system are suitable for the pediatric airway. In the pediatric airway, the position of the larynx is more anterior (forward) and cephalad, i.e., closer to the head of the patient. The epiglottis is U-shaped and more floppy than in adults. The tongue is smaller and more easily displaced. The gap between the vocal cords is narrower with the smaller size of the larynx, which results in a smaller target through which the tube must pass. In the case of a more difficult airway obstruction due to injury, for example, the difficulties involving a safe intubation of a child, a baby or a newborn infant are even more acute than in adults. The need for a good field of view and a clear image during insertion of the endotracheal tube requiring a diameter of 4 mm or less, and for verification of proper placement are further heightened.

An endotracheal tube having a diameter in a range of 3.5-4.0 mm is preferred for pediatric applications, such as babies delivered at full term, and with diameters of less than 3.0 mm preferred for premature babies. The imaging endoscope used for pediatric intubation can be larger than those previously used, as the diameter is not confined by the inner diameter of the endotracheal tube. The size of the imaging endoscope can vary between 4 mm and 11 mm depending on the size of the airway.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. An endotracheal intubation endoscope system comprising:
    an imaging endoscope having a proximal end and a steerable distal end;
    an actuator to control displacement of the steerable distal end of the imaging endoscope relative to an endoscope axis in a first direction and a second direction that is orthogonal to the first direction;
    a guide device for insertion into a subject's airway using the imaging endoscope, the actuator being used to steer the imaging endoscope to position a distal end of the guide device within the subject's airway, the guide device being positioned within, or mounted to, the imaging endoscope during insertion of the guide device and the imaging endoscope into the subject's airway, the guide device further being separable from the imaging endoscope upon insertion into the subject's airway and movable relative to the imaging endoscope such that the distal end of the guide device is moveable in a distal direction into a trachea of the subject, the distal end of the imaging endoscope being positioned to view a tracheal entry region of the subject's airway; and
    an endotracheal tube for delivery into the trachea over the guide device upon separation of the guide device from the imaging endoscope without removal of the imaging endoscope from the airway, the separated guide device being located at an endotracheal tube delivery position within the subject's airway such that the guide device and the endotracheal tube are external to, and extend alongside, the imaging endoscope within the airway, the endotracheal tube including an inflation cuff configured to be inflated within the subject's airway to form a seal with an interior wall of the trachea.

2. The system of claim 1 further comprising a release actuator that separates the distal end of the guide device from the imaging endoscope such that the distal end of the guide device is attached to the imaging endoscope during insertion into the airway and is detached with the release actuator from the imaging endoscope such that the guide device extends alongside the imaging endoscope within the airway for delivery of the endotracheal tube over the guide device.

3. The system of claim 1 further comprising an imaging detector mounted in a proximal section of the endoscope.

4. The system of claim 1 further comprising a fluid exchange system coupled to an endoscope channel.

5. The system of claim 1 wherein the imaging endoscope comprises an outer tube such that the guide device extends along a longitudinal opening in the outer tube.

6. The system of claim 1 wherein the imaging endoscope comprises an outer tube for insertion within a body cavity having a length in a range of 20 cm to 50 cm.

7. The system of claim 1 wherein the endoscope comprises a tubular body having a diameter in a range of 8 to 14 mm.

8. The system of claim 1 wherein the endoscope further comprises a light source.

9. The system of claim 2 wherein the release actuator comprises an outer tubular wall of the imaging endoscope that can be moved to open a working channel in which the guide device is positioned during insertion of the imaging endoscope into the airway.

10. The system of claim 1 further comprising a fluid delivery system coupled to a guide device lumen.

11. The system of claim 1 further comprising a light transmissive distal cap on the distal end of the imaging endoscope.

12. The system of claim 1 further comprising a retraction catheter to manipulate tissue at the distal end of the endoscope.

13. The system of claim 1 wherein the guide device comprises a second endoscope.

14. The system of claim 13 wherein the imaging endoscope provides a first image and the second endoscope provides a second image and further comprising a display that displays the first image and the second image.

15. The system of claim 1 wherein the guide device comprises a catheter.

16. The system of claim 15 wherein the catheter is steerable.

17. The system of claim 15 wherein the catheter comprises a fiber optic channel and a fluid channel.

18. The system of claim 1 wherein the inflation cuff is extendable over the guide device to a position distal to the distal end of the imaging endoscope within the airway.

19. The system of claim 1 wherein the guide device comprises a tubular body that slides within an endoscope channel prior to separation of the guide device from the endoscope channel.

20. The system of claim 1 further comprising a retraction catheter.

21. An endotracheal intubation endoscope system comprising:
an imaging endoscope having a first imaging device, the endoscope being operative to view a patient's airway;
an actuator operable to bend a distal end of the imaging endoscope relative to an axis of the imaging endoscope;
a guide endoscope movable relative to the imaging endoscope such that a distal end of the guide endoscope can be moved distally relative to the distal end of the imaging endoscope, the guide endoscope including a second imaging device to visualize entry of the guide endoscope into the trachea, the guide endoscope being positioned within, or mounted to, the imaging endoscope during insertion into the patient's airway and separated from the imaging endoscope in the patient's airway; and
an endotracheal tube having a cuff for inflation within the trachea, the endotracheal tube being configured for insertion into the patient's airway along the guide endoscope to position a distal end of the endotracheal tube within a trachea of the patient such that the cuff is inflatable to form a seal with an interior wall of the trachea, the endotracheal tube being inserted over the separated guide endoscope that is external to the imaging endoscope.

22. The system of claim 21 further comprising a directional actuator to position the distal end of the imaging endoscope in a first direction and a second direction orthogonal to the first direction.

23. The system of claim 21 further comprising a release actuator that separates the guide endoscope from the imaging endoscope upon the insertion into the patient's airway, the guide endoscope being released to a position separated from an external wall of the imaging endoscope.

24. The system of claim 21 wherein the first imaging device further comprises an imaging detector mounted in a proximal section of the imaging endoscope.

25. The system of claim 21 further comprising a fluid exchange system coupled to a channel of the guide endoscope.

26. The system of claim 21 wherein the imaging endoscope comprises an outer tube such that a guide channel extends along a longitudinal opening in the outer tube.

27. The system of claim 21 wherein the imaging endoscope comprises an outer tube for insertion within a body cavity having a length in a range of 20 cm to 50 cm.

28. The system of claim 21 wherein the imaging endoscope comprises a tubular body having a diameter in a range of 8 to 14 mm.

29. The system of claim 21 wherein the imaging endoscope further comprises a light source such that the cuff can be illuminated at a distal position relative to the distal end of the imaging endoscope.

30. The system of claim 23 wherein the release actuator comprises an outer tubular wall that can be moved to open a working channel in the imaging endoscope, the guide endoscope being positioned within the working channel.

31. The system of claim 21 further comprising a fluid delivery system coupled to a lumen of the guide endoscope.

32. The system of claim 21 further comprising a light transmissive distal cap on a distal end of the imaging endoscope.

33. The system of claim 21 further comprising a retraction catheter to manipulate tissue at the distal end of the endoscope.

34. The system of claim 21 wherein the imaging endoscope provides a first image and the guide endoscope provides a second image.

35. The system of claim 21 wherein the guide endoscope comprises a fiber optic catheter.

36. The system of claim 35 wherein the catheter is steerable.

37. The system of claim 35 wherein the catheter comprises a fiber optic channel and a fluid channel.

38. The system of claim 34 further comprising a display that simultaneously displays the first image and the second image.

39. The system of claim 21 wherein the distal end of the guide endoscope is attached to the distal end of the imaging endoscope during insertion of the imaging endoscope into the patient's airway.

40. An endotracheal intubation endoscope system comprising:
an imaging endoscope having a channel extending from a proximal end to a steerable distal end;
an actuator to control displacement of the steerable distal end of the imaging endoscope in two orthogonal directions relative to an endoscope axis;
a guide device having an imaging device for insertion into a subject's airway with the imaging endoscope, the guide device being positioned within the channel of the imaging endoscope and being separable from the imaging endoscopic upon insertion into the airway such that the guide device extends alongside the imaging endoscope within the airway without removal of the imaging endoscope after separation, the guide device being movable relative to the imaging endo scope such that a distal end of the guide device can translate in a distal direction into a trachea of the subject, the distal end of the imaging endoscope being positioned with the actuator to view tracheal entry; and
an endotracheal tube having an inflation cuff configured for inflation within the trachea, the endotracheal tube being moveable over the guide device upon separation of the guide device from the imaging endoscope to a position within the subject's airway that is external to the channel of the imaging endoscope such that inflation of the cuff forms a seal with an interior wall of the trachea.

41. The system of claim 40 wherein the actuator positions the distal end of the endoscope in a first direction and a second direction orthogonal to the first direction.

42. The system of claim 40 further comprising a release actuator that separates the distal end of the guide device from the channel of the imaging endoscope.

43. The system of claim 40 further comprising an imaging detector mounted in a proximal section or a distal section of the endoscope.

44. The system of claim 40 further comprising a fluid exchange system coupled to a second endoscope channel.

45. The system of claim 40 wherein the channel comprises an outer tube such that the guide device extends along a longitudinal opening in the outer tube during insertion into the airway.

46. The system of claim 40 wherein the imaging endoscope comprises an outer tube for insertion within a body cavity having a length in a range of 20 cm to 50 cm.

47. The system of claim 40 wherein the endoscope comprises a tubular body having a diameter in a range of 8 to 14 mm.

48. The system of claim 40 wherein the endoscope further comprises a light source.

49. The system of claim 42 wherein the release actuator comprises an outer tubular wall that can be moved to open the channel in which the guide device is positioned during insertion into the airway.

50. The system of claim 40 further comprising a fluid delivery system coupled to a guide device lumen.

51. The system of claim 40 further comprising a light transmissive distal cap on the distal end of the imaging endoscope.

52. The system of claim 40 further comprising a retraction catheter to manipulate tissue at the distal end of the endo scope.

* * * * *